US007738960B2

(12) United States Patent
Yerich et al.

(10) Patent No.: US 7,738,960 B2
(45) Date of Patent: Jun. 15, 2010

(54) SYSTEM AND METHOD FOR REMOTE PACING THRESHOLD ASSESSMENT

(75) Inventors: Charles G. Yerich, Shoreview, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 11/096,516

(22) Filed: Mar. 31, 2005

(65) Prior Publication Data
US 2006/0224205 A1 Oct. 5, 2006

(51) Int. Cl.
*A61N 1/00* (2006.01)
(52) U.S. Cl. ...................................................... 607/28
(58) Field of Classification Search .................. 607/30, 607/32, 60, 27–28, 4, 9, 50; 128/903, 904
See application file for complete search history.

(56) References Cited

U.S. PATENT DOCUMENTS

| 5,336,245 | A | * | 8/1994 | Adams et al. | 607/32 |
| 5,391,192 | A | * | 2/1995 | Lu et al. | 607/28 |
| 5,458,623 | A | * | 10/1995 | Lu et al. | 607/28 |
| 5,476,485 | A | * | 12/1995 | Weinberg et al. | 607/28 |
| 5,792,202 | A | * | 8/1998 | Rueter | 607/27 |
| 5,954,755 | A |   | 9/1999 | Cassavant | |
| 6,353,761 | B1 | * | 3/2002 | Conley et al. | 607/28 |
| 6,477,424 | B1 | * | 11/2002 | Thompson et al. | 607/60 |
| 6,804,558 | B2 | * | 10/2004 | Haller et al. | 607/30 |
| 2001/0049542 | A1 |   | 12/2001 | Florio et al. | |
| 2002/0082665 | A1 | * | 6/2002 | Haller et al. | 607/60 |
| 2002/0095190 | A1 | * | 7/2002 | Bornzin et al. | 607/28 |
| 2003/0013945 | A1 |   | 1/2003 | Graindorge et al. | |
| 2003/0045908 | A1 | * | 3/2003 | Condie et al. | 607/9 |
| 2004/0082975 | A1 | * | 4/2004 | Meyer et al. | 607/27 |
| 2004/0230244 | A1 |   | 11/2004 | Conley et al. | |

FOREIGN PATENT DOCUMENTS

EP 0761255 3/1997
EP 1222942 7/2002

* cited by examiner

*Primary Examiner*—Mark W Bockelman
(74) *Attorney, Agent, or Firm*—Stephen W. Bauer

(57) ABSTRACT

A cardiac rhythm management system includes an implantable medical device capable of delivering cardiac therapy and sensing an EGM. The implantable medical device undergoes threshold testing and transmits testing data to a computer via a remote monitor.

18 Claims, 3 Drawing Sheets

SYSTEM AND METHOD FOR REMOTE PACING THRESHOLD ASSESSMENT

The present invention relates to cardiac pacing systems, and more particularly to a system and method for remote cardiac pacing threshold assessment.

Cardiac pacing can be delivered to a patient's heart by an implantable medical device (IMD) capable of sensing electrical activity of the heart and providing pacing at desired locations using one or more pacing leads. For instance, using cardiac resynchronization therapy (CRT), the ventricles can be paced simultaneously, or one ventricle can be paced slightly before the other. With bi-ventricular pacing, the IMD paces or senses atrial depolarizations, waits a predetermined time (or atrioventricular (AV) delay) after each sensed or paced atrial depolarization, and then paces both ventricles.

Cardiac pacing threshold testing is conducted to assess whether a pacemaker or other IMD having pacing capabilities is functioning properly. Threshold testing determines how large the pacing pulse must be to pace the heart. Pacing thresholds can vary for numerous reasons. Patient activities (such as eating) and patient conditions (increases and/or decreases in vagal and/or sympathetic stimulation) may cause these thresholds to vary on a daily basis. Electrolyte imbalance and other health events can cause thresholds to change. Over time, thresholds can also vary as the lead electrode-tissue interface matures or due to undesired movement of the pacing lead relative to the heart.

Threshold margin testing allows a safety margin to be set for the pacing pulse amplitude and pulse width, which enables adequate pacing despite variations in pacing thresholds. A typical safety margin is 100% (e.g., pulse amplitude is twice the pacing threshold amplitude or the pulse width is three times the pacing threshold pulse width).

In conducting threshold testing of prior pacing systems, trans-telephonic monitoring (TTM) is conducted using a magnet and electrocardiogram (ECG) electrodes. The patient begins the process by calling a technician to coordinate the threshold testing procedure. ECG electrodes are placed on the patient's wrists to record electrical activity. The magnet is placed near the implanted pacing device to activate a testing mode of the implanted device. Testing involves sending test pulses of reduced pulse width to the heart while recording an ECG. Some time after testing data is gathered, pacing thresholds are determined through visual analysis of sensed ECG waveforms. Loss of capture of the pacing system at a reduced pulse width is determined by analyzing, for example, ECG waveform shapes.

Administering TTM threshold tests has involved a great deal of supervision by trained technicians. Patients also must be able to understand and actively coordinate the testing procedure by properly positioning the ECG electrodes to record testing data and properly positioning the magnet to trigger testing. The testing is burdensome to patients, and does not permit immediate analysis of pacing thresholds. As a result, threshold testing is typically conducted no more than a few times per year.

BRIEF SUMMARY OF THE INVENTION

The present invention provides improved pacing threshold assessment with an IMD capable of delivering cardiac therapy and sensing an EGM. The implantable medical device undergoes threshold testing and transmits testing data to a computer via a remote monitor.

DETAILED DESCRIPTION

Figure 1:
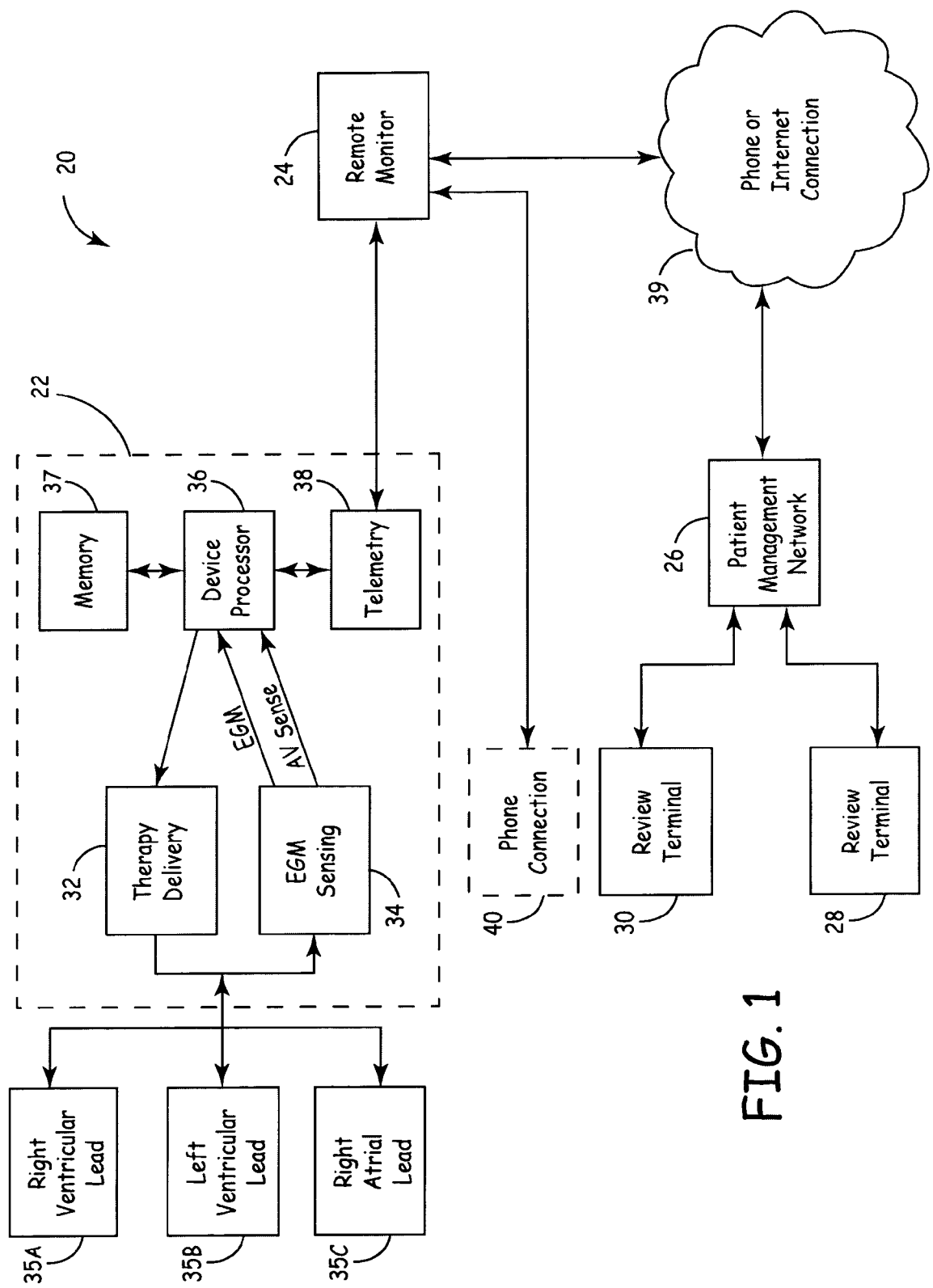
FIG. 1 is a schematic representation of a cardiac rhythm management system.

FIG. 1 is a schematic representation of cardiac rhythm management system 20, which includes implantable medical device (IMD) 22, remote monitor 24, patient management network 26, and review terminals 28 and 30. System 20 provides cardiac therapy and is capable of conducting remote pacing threshold testing of IMD 22.

IMD 22 can be a pacemaker, defibrillator, cardioverter, cardioverter-defibrillator, heart function monitor having pacing capabilities, or an equivalent cardiac system management device. IMD 22 includes therapy delivery circuitry 32 and electrogram (EGM) sensing circuitry 34, both operatively connected to right ventricular, left ventricular, and right atrial leads 35A, 35B, and 35C, respectively. EGM sensing circuitry 34 can perform functions such as analog-to-digital conversion, signal amplification, and peak sensing, and threshold measurement. Therapy delivery circuitry 32 and EGM sensing circuitry 34 are controlled by device processor 36. Memory 37 is provided for storing sensed data. IMD 22 communicates externally via telemetry 38.

Leads 35A, 35B, and 35C are positioned to provide pacing pulses and sense electrical activity at desired locations in or on the patient's heart. It will be recognized by those skilled in the art that electrode assemblies can be positioned at various locations that depend upon the type of therapy provided to the patient. Each lead 35A, 35B, and 35C can include multiple sense/pace electrodes, as well as defibrillation coil electrodes. EGM data is sensed by measuring voltage differentials between any pair of EGM sensing electrodes (e.g., tip-to-coil, tip-to-ring, and tip-to-can EGM sensing).

Remote monitor 24 is a computer or programmer that communicates with IMD 22 by telemetry, and is connected to patient management network 26 by phone or Internet connection 39. Remote monitor 24 is typically located in the patient's home, and can interrogate IMD 22. For instance, remote monitor 24 can initiate testing of IMD 22 at night, while the patient is sleeping, without any direct activation by the patient. An optional phone connection 40 can be provided with remote monitor 24 for communicating with a technician or clinician (e.g., via a "help line" or similar support system).

Patient management network 26 can include an Internet-accessible server that is connected (through a local area network, the Internet, etc.) to computers that function as review terminals 28 and 30. Data from IMD 22 can be transmitted to patient management network 26 via remote monitor 24, and can be stored in a database on network 26. Terminals 28 and 30 permit patients, healthcare providers, and technicians to access patient data to monitor pacing threshold testing on a substantially real-time basis. Testing data may be used, for example, to set and adjust the pacing safety margin.

In operation, IMD 22 paces the heart by providing electrical pulses to one or more locations of the heart. With bi-ventricular pacing, pacing leads 35 and 35B are positioned relative to the heart to pace both the left and right ventricles. Pulses are provided at a selected pulse width, a selected pulse amplitude (e.g., 3 volts), and according to a timing schedule determined as a function of the cardiac therapy desired.

Cardiac pacing threshold margin testing is conducted to determine how large the pulse width must be to pace the heart. A safety margin for pacing pulses delivered by IMD 22 may be set at 100%, although other safety margins can be selected.

A threshold testing protocol can be initiated by IMD 22, remote monitor 24, patient management network 26, or terminals 28 and 30 connected to the patient management network 26. Typically, testing is automatically initiated by system 20 on a periodic basis (e.g., once a day at a time when the patient is at rest) without any action by the patient. Testing can also be prompted at any time by the patient, a technician, or a healthcare provider, such as in response to problems experienced by the patient. A threshold testing protocol consists of providing pulses at an overdrive rate (e.g., providing about 100 pulses per minute (ppm)) and reducing pulse width on particular pulses. For example, a threshold testing protocol can involve providing a series of pulses for a period of about 10 seconds, where pulse width is reduced by 25% on the third pulse, reduced by 50% on the fifth pulse, reduced by 75% on the seventh pulse, and provided at 100% pulse width on all other pulses. Cardiac therapy can be maintained or suspended during threshold testing. For instance, if bi-ventricular pacing is provided with an offset between pacing to the left and right sides of the heart, the pacing offset can be maintained during threshold testing. In addition, system 20 can force pacing to conduct threshold testing.

If a communication breakdown between IMD 22 and remote monitor 24 occurs during threshold testing, IMD 22 defaults to a normal operation mode to provide cardiac therapy in the usual manner. This reduces the likelihood of IMD 22 becoming locked in a non-restorable state.

EGM signals are sensed by EGM sensing circuitry 34 during threshold testing, are digitized and stored in memory 37. The best vector for obtaining EGM data at a desired location (e.g., left or right ventricle or right atrium) is selected. For example, if left-side heart pacing thresholds are desired, EGM sensing electrodes at or near the left side of the heart are selected (e.g., a left ventricular tip-to-can EGM source), and likewise for right-side heart locations. Generally, loss of capture (or a no-capture result) is indicated by deviations from normal, anticipated EGM waveform shapes. Loss of capture indicates that the pulse width is below the pacing threshold.

As an alternative to initiating a threshold testing protocol, threshold testing can take place based upon EGM data sensed during normal pacing by IMD 22. In this manner, testing can occur through a program routine of IMD 22 that detects a loss of capture during normal cardiac therapy operations. An EGM source can be temporarily programmed to sense threshold test data at a particular location (e.g., a left or right ventricle or across both ventricles) during normal pacing.

System 20 permits remote pacing threshold assessment via home interrogation of IMD 22. With bi-ventricular pacing therapies, system 20 can pace or test the right and left ventricles separately or together.

Figure 2:
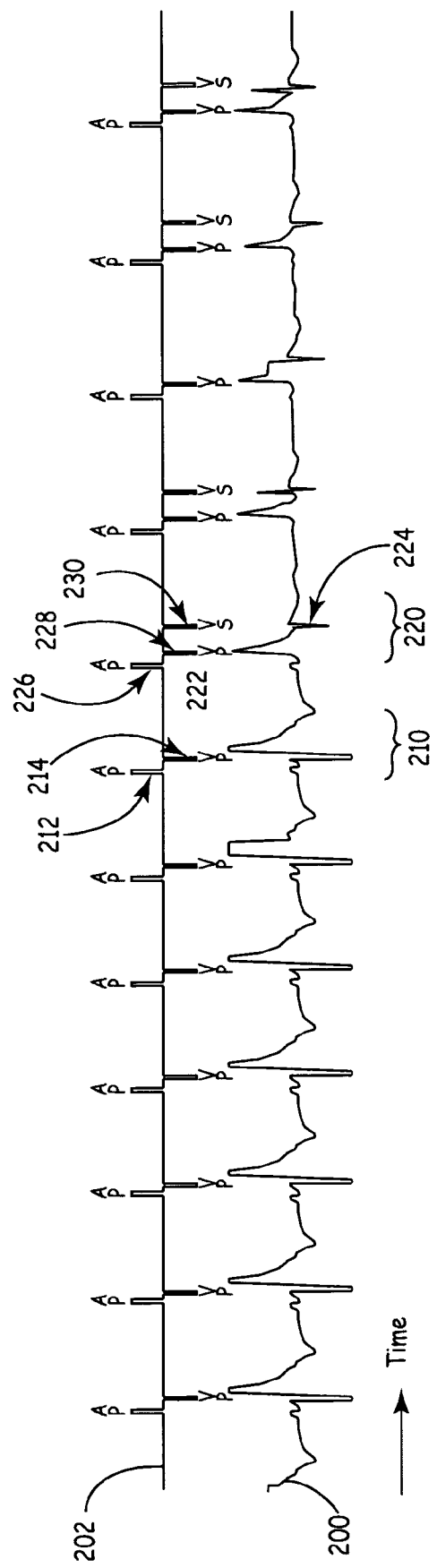
FIG. 2 is a representation of threshold testing data for right heart pacing by the cardiac rhythm management system of FIG. 1.
Figure 3:
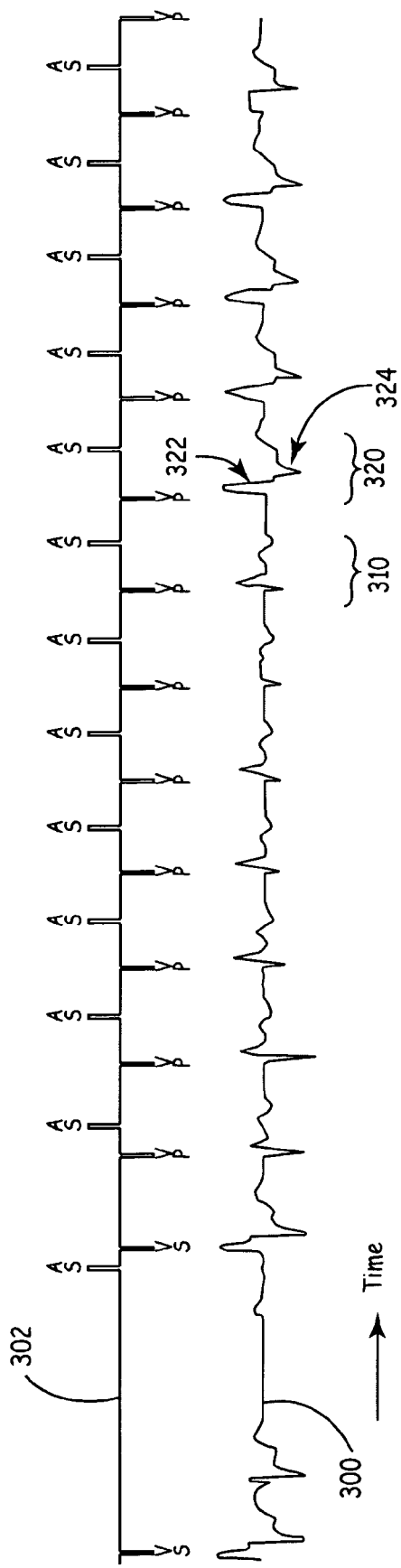
FIG. 3 is a representation of threshold testing data for bi-ventricular pacing by the cardiac rhythm management system of FIG. 1.

FIGS. 2 and 3 illustrate examples of pacing threshold testing data. FIG. 2 is a representation of threshold testing data for right heart pacing by the cardiac rhythm management system 20. In this example, right ventricle threshold testing was conducted at a 70 ppm overdrive rate with a nominal pulse amplitude of 3 volts and EGM sensing from right ventricle tip to right ventricle coil. The testing data includes EGM waveform 200 and annotation waveform 202, which is an output provided by IMD 22 that identifies occurrences of pacing and sensing events present in the EGM data and is synchronized with EGM waveform 200. In further embodiments, annotation waveform 202 can include an indication of pulse width.

EGM waveform 200 depicts amplitude of electrical activity over time. Time interval 210 of EGM waveform 200 illustrates normal pacing capture, which corresponds to indications in annotation waveform 202 showing atrial pace (AP) event 212 followed by ventricular pace (VP) event 214.

Time interval 220 of EGM waveform 200 illustrates a loss of capture. In EGM waveform 200, waveform feature 222 is followed by sharp deflection feature 224. In annotation waveform 202 during time interval 220, AP event 226 is followed by VP event 228 (corresponding to waveform feature 222) and then ventricular sense (VS) activity 230 (corresponding to sharp deflection feature 224). During time interval 220, the pulse width of the pacing pulse provided was below the pacing threshold, which led to the occurrence of delayed electrical activation of the right ventricle via atrioventricular conduction after the pacing pulse. A pacing threshold for the pacing configuration can be determined based upon the pulse widths provided and the resulting capture or loss of capture determination at those pulse widths.

FIG. 3 is a representation of threshold testing data for bi-ventricular pacing by the cardiac rhythm management system 20. In this example, right and left ventricle threshold testing was conducted at a 90 ppm overdrive rate with a nominal pulse amplitude of 3 volts and EGM sensing from left ventricle tip to right ventricle coil. The testing data includes EGM waveform 300 and annotation waveform 302, similar to that shown and described with respect to FIG. 2. In EGM waveform 300, time interval 310 illustrates normal two-site pacing capture for both sides of the heart.

In contrast, time interval 320 of EGM waveform 300 illustrates a loss of capture for one side of the heart. EGM waveform 300 includes waveform feature 322, which corresponds to an increase in amplitude of electrical activity, followed by sharp deflection feature 324, which corresponds to delayed depolarization of one side of the heart. During time interval 320, pacing of one of the two ventricles was captured, and depolarization propagated over the heart and appears in the other ventricular chamber at a later time.

With bi-ventricular threshold testing, EGM data allows detection of a loss of capture in one of the two pacing locations. In order to determine which of the pacing leads lost capture, EGM testing data can be compared to known patient records corresponding to a loss of capture at a particular pacing location. Alternatively, further threshold testing can be conducted to isolate the pacing location where loss of capture occurred (e.g, by threshold testing one ventricle at a time).

The capture/no-capture results shown and described with respect to FIGS. 2 and 3 are provided by way of example, and not limitation. Other capture/no-capture results can be detected using system 20. The particular EGM data features indicating no-capture results will vary according to the type of therapy delivered and the EGM vector selected for analysis.

EGM waveforms are visually analyzed by a qualified interpreter, such as a physician. In another embodiment, remote monitor 24, patient information network 26, or review terminals 28 and 30 provide automatic waveform analysis of EGM waveforms and corresponding annotations to detect capture/no-capture results. Automatic notification of a no-capture result could then be provided to the patient and/or the patient's caregivers (e.g., through indicator lights on remote monitor 24 or via a phone message or e-mail from patient information network 26 or review terminals 28 or 30) and to the clinician via patient management network 26. When a no-capture result is detected or recorded, the healthcare provider can then look at the testing data to assess the safety margin and make adjustments as needed. Generally, this means increasing the safety margin, which can be done remotely by providing new settings from remote monitor 24 to telemetry circuit 38 of IMD 22 or through a device programmer at an in-office visit. With automatic waveform analysis, system 20 can provide recommendations corresponding to pacing threshold determinations and can automatically adjust pacing margins as desired by the caregiver.

Thus, the cardiac rhythm management system of the present invention permits remote cardiac pacing threshold assessment without the need for ECG electrodes or the direct assistance of medical personnel. The system can force pacing, and electrical activity data sensed by the IMD is used to analyze pacing thresholds at any time on a substantially real-time basis. The testing can be initiated automatically and remotely, and active participation by the patient to activate testing is not required (though a person can activate on-the-spot testing, if desired). Testing can even occur without the patient being aware of it. Pacing threshold data can be collected easily on a regular basis. Testing data can be compiled in a patient registry for one or more patients, permitting trend data to be collected and analyzed, as desired.

Although the present invention has been described with reference to preferred embodiments, workers skilled in the art will recognize that changes may be made in form and detail without departing from the spirit and scope of the invention.

The invention claimed is:

1. A cardiac rhythm management system comprising:
   an implantable medical device capable of delivering cardiac pacing therapy and sensing EGM signals and producing EGM waveform data, the IMD being programmed to perform cardiac pacing threshold testing, during which test data including EGM waveform data is obtained;
   an external monitor communicating with the implantable medical device by telemetry and initiating the implantable medical device to perform the pacing threshold testing and receiving the test data including the obtained EGM waveform data; and
   a computer remote from the external monitor operatively connected to the monitor and causing the monitor to initiate the implantable medical device to perform the threshold testing and receiving the test data from including the obtained EGM waveform data from the monitor wherein said initiating can be performed automatically and remotely.

2. A cardiac rhythm management system comprising:
   an implantable medical device capable of delivering cardiac pacing therapy and sensing EGM signals and producing EGM waveform data, the IMD being programmed to perform cardiac pacing threshold testing, during which test data including EGM waveform data is obtained;
   an external monitor communicating with the implantable medical device by telemetry and initiating the implantable medical device to perform the pacing threshold testing and receiving the test data including the obtained EGM waveform data; and
   a computer remote from the external monitor operatively connected to the monitor and causing the monitor to initiate the implantable medical device to perform the threshold testing and receiving the test data from including the obtained EGM waveform data from the monitor; and
   wherein the computer is programmed to automatically determine a cardiac pacing threshold value from the test data including the obtained EGM waveform data and adjust the IMD pacing margins.

3. The system of claim 1 or claim 2, wherein the computer is operatively connected to the monitor through a phone or Internet connection.

4. The system of claim 1 or claim 2, wherein the monitor records the test data received from the implantable medical device.

5. The system of claim 1 or claim 2, wherein the implantable medical device is selected from the group consisting of: a pacemaker, a defibrillator, an implantable cardioverter-defibrillator, and an implantable heart function monitor having pacing capabilities.

6. The system of claim 1 or claim 2, wherein the test data is displayed by the computer on a substantially real-time basis during threshold testing.

7. The system of claim 1 or claim 2, wherein the test data is stored by the computer in a patient registry database.

8. The system of claim 1 or claim 2, wherein the implantable medical device provides bi-ventricular pacing while cardiac pacing threshold testing is conducted.

9. The system of claim 1 or claim 2 wherein the implantable medical device detects loss of capture during the pacing threshold testing.

10. A cardiac rhythm management method comprising:
    employing an implantable medical device capable of delivering cardiac pacing therapy and sensing EGM signals and producing EGM waveform data, to perform cardiac pacing threshold testing, during which test data including EGM waveform data is obtained;
    employing a remote monitor to initiate the implantable medical device to perform the pacing threshold testing and to receive the test data including the obtained EGM waveform data; and
    employing a computer operatively connected to the remote monitor to cause the remote monitor to initiate the implantable medical device to perform the threshold testing and to receive the test data including the obtained EGM waveform data from the remote monitor wherein said initiating can be performed automatically and remotely.

11. A cardiac rhythm management method comprising:
    employing an implantable medical device capable of delivering cardiac pacing therapy and sensing EGM signals and producing EGM waveform data, to perform cardiac pacing threshold testing, during which test data including EGM waveform data is obtained;
    employing a remote monitor to initiate the implantable medical device to perform the pacing threshold testing and to receive the test data including the obtained EGM waveform data; and
    employing a computer operatively connected to the remote monitor to cause the remote monitor to initiate the implantable medical device to perform the threshold testing and to receive the test data including the obtained EGM waveform data from the remote monitor; and
    employing the computer to automatically determine a cardiac pacing threshold value from the test data including the obtained EGM waveform data and adjust the IMD pacing margins.

12. The method of claim 10 or claim 11, comprising operatively connecting the computer to the remote monitor through a phone or Internet connection.

13. The Method of claim 10 or claim 11, comprising employing the remote monitor to record the test data received from the implantable medical device.

14. The method of claim 10 or claim 11, comprising selecting the implantable medical device from the group consisting of: a pacemaker, a defibrillator, an implantable cardioverter-defibrillator, and an implantable heart function monitor having pacing capabilities.

15. The method of claim 10 or claim 11, comprising employing the computer to display the test data on a substantially real-time basis during threshold testing.

16. The method of claim 10 or claim 11, comprising employing the computer to store the test data in a patient registry database.

17. The method of claim 10 or claim 11, comprising employing the implantable medical device to provide bi-ventricular pacing while cardiac pacing threshold testing is conducted.

18. The method of claim 10 or claim 11, comprising employing the implantable medical device to detect loss of capture during the pacing threshold testing.

* * * * *